(12) United States Patent
Kasper et al.

(10) Patent No.: US 9,404,517 B2
(45) Date of Patent: Aug. 2, 2016

(54) LATCHING APPARATUS AND ALSO MEDICAL IMAGING APPARATUS WITH THE LATCHING APPARATUS

(75) Inventors: Peter Kasper, Seon (CH); Bernd Maciejewski, Markt Erlbach (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 273 days.

(21) Appl. No.: 13/603,525

(22) Filed: Sep. 5, 2012

(65) Prior Publication Data
US 2013/0236241 A1 Sep. 12, 2013

(30) Foreign Application Priority Data
Sep. 8, 2011 (DE) .......... 10 2011 082 369

(51) Int. Cl.
| | |
|---|---|
| F16B 2/00 | (2006.01) |
| F16B 2/22 | (2006.01) |
| G01R 33/38 | (2006.01) |
| G01R 33/28 | (2006.01) |
| A61B 5/055 | (2006.01) |

(52) U.S. Cl.
CPC . *F16B 2/22* (2013.01); *A61B 5/055* (2013.01); *G01R 33/28* (2013.01); *G01R 33/3802* (2013.01); *Y10T 292/0824* (2015.04); *Y10T 403/602* (2015.01)

(58) Field of Classification Search
CPC ............. F16B 2/20; F16B 2/22; F16B 2/248; F16B 2/16; F16B 2/24; Y10T 403/591; Y10T 292/0824; Y10T 292/0902; Y10T 292/096; Y10T 403/599; G01R 33/3802

USPC ............ 292/9, 12, 23, 80, DIG. 11, DIG. 61; 403/327; 312/222
See application file for complete search history.

(56) References Cited

U.S. PATENT DOCUMENTS

| | | | | |
|---|---|---|---|---|
| 831,367 | A * | 9/1906 | Morris et al. .................. | 24/488 |
| 2,215,914 | A * | 9/1940 | Coffey ............................ | 292/45 |
| 2,502,607 | A * | 4/1950 | Vinton .......................... | 292/23 |
| 2,941,831 | A * | 6/1960 | Borsani ........................ | 292/79 |
| 3,287,043 | A * | 11/1966 | Delhase .......................... | 292/9 |
| 3,450,851 | A * | 6/1969 | Perl ............................ | 200/61.68 |
| 4,215,884 | A * | 8/1980 | Little .......................... | 292/220 |
| 4,470,180 | A * | 9/1984 | Blomgren ....................... | 24/563 |
| 4,901,402 | A * | 2/1990 | Begemann .................... | 24/129 D |
| 5,595,426 | A * | 1/1997 | Wolff et al. ................... | 312/109 |
| 7,611,213 | B2 * | 11/2009 | Wu et al. .................. | 312/334.44 |
| 7,905,524 | B2 * | 3/2011 | Migli ............................ | 292/220 |
| 8,123,312 | B2 * | 2/2012 | Jeon et al. ..................... | 312/228 |
| 8,536,864 | B2 * | 9/2013 | Kasper et al. ................. | 324/300 |
| 2006/0108480 | A1 * | 5/2006 | Goodwin et al. .............. | 248/63 |

(Continued)

FOREIGN PATENT DOCUMENTS

| | | |
|---|---|---|
| CN | 101509963 A | 8/2009 |
| DE | 102008003779 A1 | 7/2009 |
| DE | 102009023858 A1 | 12/2010 |

(Continued)

*Primary Examiner* — Daniel P Stodola
*Assistant Examiner* — Matthew R McMahon

(57) ABSTRACT

A latching apparatus for housing cladding of a medical imaging device is provided. The latching apparatus has at least one first cladding component, a second cladding component and at least one latching unit. The at least one latching unit is disposed entirely on the first cladding component for a latching connection with the at least one second cladding component.

14 Claims, 4 Drawing Sheets

(56) References Cited

U.S. PATENT DOCUMENTS

2008/0306369 A1* 12/2008 Udupa .................... 600/407
2009/0200905 A1* 8/2009 Gore et al. .................... 312/400

FOREIGN PATENT DOCUMENTS

| DE | 102010032321 A1 | 2/2012 |
|---|---|---|
| GB | 2457446 A | 8/2009 |

* cited by examiner

US 9,404,517 B2

LATCHING APPARATUS AND ALSO MEDICAL IMAGING APPARATUS WITH THE LATCHING APPARATUS

CROSS REFERENCE TO RELATED APPLICATIONS

This application claims priority of German application No. 10 2011 082 369.7 filed Sep. 8, 2011, which is incorporated by reference herein in its entirety.

FIELD OF INVENTION

The present application relates to a latching apparatus, such as for housing cladding of a medical imaging apparatus, with at least one first cladding component and at least one second cladding component and at least one latching unit.

BACKGROUND OF INVENTION

Various demands in respect of design, service and safety are imposed on the housing cladding for the layout of housing cladding, such as for medical imaging devices such as magnetic resonance apparatuses or computed tomography apparatuses etc. Thus for example, because of design aspects, no screw connections of the housing cladding should be visible from the outside. However, because of service aspects, all cladding components of the housing cladding should still be disposed to allow easy installation and dismantling. In addition, because of safety aspects, such as in respect of accessibility to electronic components, the cladding components should be able to be installed and dismantled with just one tool.

With cladding components having a large surface area, these requirements can lead to a conflict, since these large-surface cladding components, because of their weight, are to be securely disposed, such as on the one hand being securely screwed on for example. On the other hand, because of accessibility to electronic components, these large-surface cladding components should also be able to be dismantled in a very short time. These requirements have thus far only been met in an unsatisfactory manner by using commercially-available screw connections to attach the cladding components and screwing the cladding components to the medical imaging apparatus.

SUMMARY OF INVENTION

The underlying object of the present application is to provide a latching apparatus by which a cost effective and constructively simple latching connection is achieved between the individual cladding components of a medical imaging apparatus. The object is achieved by the features of the independent claims. Embodiments are described in the dependent claims.

The application is based on a latching apparatus for housing cladding of a medical imaging apparatus with at least one first cladding component, at least one second cladding component and a latching unit.

It is proposed that the at least one latching unit is disposed entirely on the first cladding component for a latching connection with the at least one second cladding component. This enables housing cladding to be disposed in a constructionally simple manner around a detector unit of a medical imaging apparatus. In addition, as a result of the latching unit, it is simple to dismantle the cladding components for service work for example. Furthermore the latching unit can be disposed in this way in a compact manner within the latching apparatus, in which case additional installation steps and costs can be saved here because of the simple arrangement on only one cladding component. Operation of the latching apparatus without tools can be achieved which, because of the latching connection, makes it possible to easily install or dismantle cladding components at any time.

It is further proposed that the at least one latching unit has a latching spring with a latching wheel, through which a latching force can be provided for a latching connection as a result of the pre-tensioning of the latching spring. In addition, by the latching wheel, as a result of a rotational movement performed by the latching wheel, installation and/or dismantling of cladding components in an installation direction and/or in a dismantling direction can be supported.

The latching wheel can be held in a latching position for a latching connection with the at least one second cladding component, if the latching wheel is supported rotatably on the latching spring. The latching wheel is able to be rotated around an axis which is aligned in parallel to a longitudinal extent of a part area of the latching spring on which the latching wheel is supported. In addition a latching movement and/or a movement to release a latching connection can be supported as a result of the rotatably supported latching wheel and in this way installation and/or dismantling of cladding components can be designed in a user-friendly manner.

It is further proposed that the latching wheel has at least two spokes and at least two cutouts, with the at least two spokes and the at least two cutouts being disposed in a radial direction around an opening of the latching wheel for support on the latching spring. This allows the latching unit to be manufactured easily and with cost savings, by the latching wheel being able to be attached to the latching spring during manufacturing of the latching unit after bending and/or shaping of the latching spring, wherein by the at least two cutouts, movement of the latching wheel is also possible along the latching spring in curved areas of the latching spring. In addition the at least two spokes can assist a play-free positioning of the latching wheel in a latching position on the latching spring and/or a play-free movement of the latching wheel on the latching spring, by the spokes being able to rest at least partly on the latching spring. The opening of the latching wheel through which the latching spring is guided for support of the latching wheel on the latching spring is disposed centrally within the latching wheel. In addition to this, the latching wheel can be embodied on both latching wheel disk surfaces in respect of an arrangement of grooves and spokes similarly and/or symmetrically, so that a thickness of the latching wheel, such as a thickness of a latching wheel disk, can be embodied thin and in this way a sliding of the latching wheel during installation of the latching wheel on the latching spring, in curved areas and/or bends of the latching spring can be achieved. This also enables hindering of a sliding movement of the latching wheel on the latching spring by the spokes, as would occur with a non-symmetrical arrangement of the spokes between the two latching disk surfaces in curved areas of the latching spring and/or in bends of the latching spring, to be prevented.

If the latching spring has a safety area which restricts the maximum latching movement of the latching spring, an over tensioning of the latching spring and/or a mispositioning of the latching wheel for a latching position can be prevented. The safety area of the latching spring can for example be formed by an area which in a latching movement of the latching spring forms an angle to a direction of movement of the latching movement of the latching spring, wherein the angle is greater than 90° and greater than 120°. In addition the angle is smaller than 165° and smaller than 160°, so that a latching movement of the latching spring, for example in a guide channel, can only occur along a permitted area and a movement beyond the intended latching movement can be prevented by the safety area. In this case a latching movement should be understood as a movement of the latching spring which the latching spring performs to make or to release a latching connection with a further cladding component.

In a development of the application it is proposed that the latching unit has a base unit for supporting the latching spring, through which the latching spring can be supported independently of an embodiment of the at least one first cladding component for a latching connection. The latching unit has an attachment unit for this purpose, by which the latching spring can be attached to the base unit, so that the latching spring, such as during a latching process, can be supported or disposed on the base unit in a captive manner.

The base unit is fixed to the at least one first cladding component so that a precisely-positioned support of the latching spring on the first cladding component can be achieved for a latching connection and in this way a tightly fitting arrangement of the at least two cladding components within the housing cladding can be achieved. In addition imprecise arrangements of cladding components, in which for example the cladding components are separated from one another by large gaps, can be prevented.

For fixed, immovable support of at least one part area of the latching spring the base unit has at least one first guide element, so that the latching spring can always be supported here in an optimum latching position. In addition the latching forces which are transmitted to the latching spring for making and/or releasing a latching connection are conducted away in this case via the first guide element to the base unit and if necessary to the first cladding component, and in this way latching spring wear is minimized. In this context a fixed support of the latching spring should be understood as the latching spring, the part area of the latching spring supported in the guide element, being supported in this first guide element immovably relative to the base unit.

Furthermore it is proposed that the base unit has at least one second guide element for mobile support of at least one part area of the latching spring, through which the latching spring can perform a predetermined movement sequence for a latching movement. In addition a movement of the latching spring deviating from the latching movement can be prevented in this case and by association a long life of the latching spring can be achieved as a result of avoiding overtensioning of the latching spring. In addition, as a result of an embodiment of the guide element, a length of a latching movement can be set and by association a latching force or spring force of the latching spring can be set.

In an alternative embodiment of the application it is proposed that the base unit has a height which is adapted at least to a spacing of an edge area of the at least one second cladding component to a cladding surface of the at least one first cladding component facing towards the base unit so that a position of the latching spring and of the latching wheel can be adapted to a position of the at least one second cladding component making a latching connection with the latching wheel in a constructively simple manner. In addition tolerances in a thickness of the first cladding component and/or the second cladding component can be compensated for in this way. In this case a distance between an edge area of the at least one second cladding component and a cladding surface facing the base unit of the at least one first cladding component is to be understood as a distance which this edge area at a rim area facing away from the first cladding component has to the cladding surface of the first cladding component facing towards the base unit.

In addition it is proposed that the base unit has at least one positioning element for positioning the latching wheel on the latching spring, through which the latching wheel can be supported in a latching position on the latching spring and in addition a mispositioning of the latching wheel on the latching spring can be prevented.

In addition it is proposed that, in a locking position, the latching wheel makes a latching connection with the at least one second cladding component. In this case a connection between the latching unit and the at least one second component can be achieved, wherein a stability of this connection can depend on a latching force and/or on an embodiment of the latching unit, such as of the latching spring. For example the connection between the latching unit and the at least one second cladding component can be formed by a latching connection supporting an attachment of the second cladding component, so that a number of attachment elements, such as attachment screws etc., for attaching the least one second cladding component, can be restricted to a minimum. If on the other hand the latching spring is embodied such that a cross-section of the latching spring is greater by approximately 10% than a cross section in an embodiment of the latching spring for a supporting latching connection, a greater latching force between the latching unit and the at least one second cladding component can be created and in this way additional attachment elements dispensed with.

It is further proposed that, in the locking position, the latching wheel has a overlap area with the at least one second cladding component, wherein the overlap area is greater than 25% of the outer diameter of the latching wheel and less than 50% of the outer diameter of the latching wheel. In this case the latching wheel can overlap the at least one second cladding component far enough for a secure latching connection and in addition during a release of the latching connection by pulling away the at least one first cladding unit, a force is transferred to the latching wheel which leads to a movement of the latching spring along a latching movement. Furthermore this enables damage to the latching spring and/or the latching wheel to be prevented during release of the latching connection between the latching unit and the at least one second cladding component.

Use of the latching apparatus for housing cladding within a magnetic resonance apparatus can be achieved if the latching unit is embodied to be compatible with magnetic resonance.

The disclosed latching apparatus is suitable for attachment of large-surface cladding components, as can be used in the housing cladding of medical imaging devices, such as magnetic resonance devices. In this way a housing cladding and/or a medical imaging apparatus, especially a magnetic resonance apparatus, can be obtained in which the individual cladding components can be disposed simply and with little effort within the housing cladding. In this case thin-wall cladding components can also be disposed within the housing cladding and in such cases undesired distortion of the individual cladding components can be prevented.

BRIEF DESCRIPTION OF THE DRAWINGS

Features and details of the application emerge from the embodiments described below and also with reference to the drawings, in which.

DETAILED DESCRIPTION OF INVENTION

Figure 1:
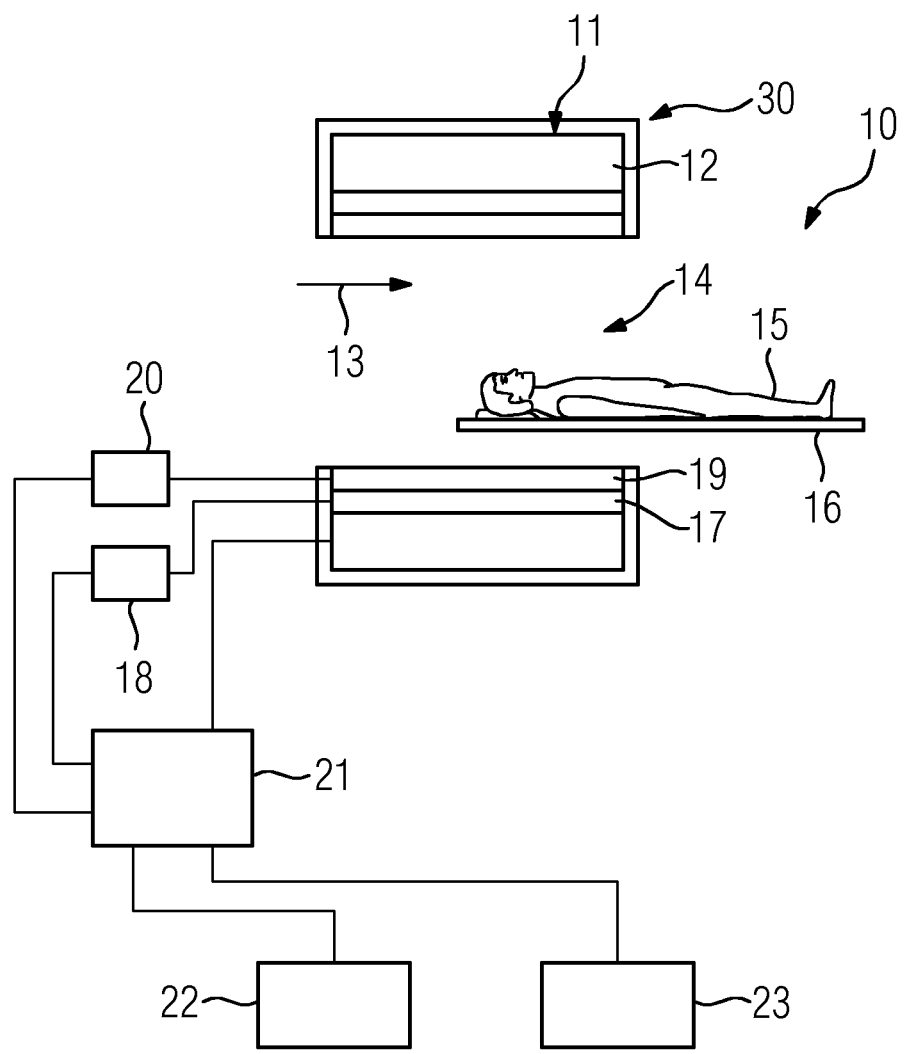
FIG. 1 shows a schematic of a magnetic resonance apparatus.

FIG. 1 shows a schematic of a disclosed medical imaging apparatus which is formed by a magnetic resonance apparatus 10. As an alternative to this the medical imaging apparatus can also be formed by a CT apparatus or a PET apparatus and/or by further medical apparatuses appearing sensible to the person skilled in the art.

The magnetic resonance apparatus 10 comprises a magnet unit 11 with a main magnet 12 for generating a strong and constant main magnetic field 13. In addition the magnetic resonance apparatus 10 has a cylindrical receiving area 14 for receiving a patient 15, wherein the receiving area 14 is enclosed in a circumferential direction by the magnet unit 11. The patient 15 can be introduced by a patient couch 16 of the magnetic resonance apparatus 10 into the receiving area 14. The patient couch 16 is disposed for this purpose movably within the magnetic resonance apparatus 10. Furthermore the magnetic resonance apparatus 10 has housing cladding 30 surrounding the magnet unit 11.

The magnet unit 11 also has a gradient coil 17 for generating magnetic field gradients which are used for local coding during imaging. The gradient coil 17 is controlled by means the gradient control unit 18. Furthermore the magnet unit 11 has a high-frequency antenna 19 and a high-frequency antenna unit 20 for exciting a polarization which is set in the main magnetic field 13 generated by the main magnet 12. The high-frequency antenna 19 is controlled by the high-frequency antenna unit and emits high-frequency magnetic resonance sequences into an examination area which is formed by the receiving area 14. This deflects the magnetization from its position of equilibrium. In addition magnetic resonance signals are received by the high-frequency antenna unit 20.

For control of the main magnet 11, the gradient control unit 18 and for control of the high-frequency antenna unit 20, the magnetic resonance apparatus 10 has a control unit 21 formed by a processing unit. The processing unit centrally controls the magnetic resonance apparatus 10, such as for example the carrying out of a predetermined imaging gradient echo sequence. Control information such as imaging parameters for example, and also reconstructed magnetic resonance images, can be displayed on a display unit 22 for example on at least one monitor of the magnetic resonance apparatus 10. In addition the magnetic resonance apparatus 10 has an input unit 23, by which the information and/or parameters can be entered by an operator during a measurement process.

The magnetic resonance apparatus 10 shown can naturally comprise further components that magnetic resonance apparatuses 10 normally feature. The general manner in which a magnetic resonance apparatus 10 functions is also known to the person skilled in the art, so that the general components will not be described in any greater detail here.

The disclosed latching apparatus 31, which is enclosed by the housing cladding 30, is described in greater detail in FIGS. 2 to 7. The latching apparatus 31 comprises a first cladding component 32, a second cladding component 33 and a number of latching units 34, wherein FIG. 2 through 7 only show one of the latching units 34 by way of example. A number of the latching units 34 within the latching apparatus 31 can depend in such cases on the size and/or weight and/or position of the individual cladding components 32, 33 and/or on an embodiment of the housing cladding 30.

The first cladding component 32 is attached to the second cladding component 33 by the latching units 34 or the first cladding component 32 is held in an attachment position on the second cladding component 33. For this purpose the latching units 34 are disposed entirely on the first cladding unit 32. For disposal of the latching units 34 in a magnetic resonance apparatus 10 the latching units 34 are embodied to be compatible with magnetic resonance. The cladding components 32, 33 are each formed by large-area shell elements of the housing cladding 30.

The latching unit 34 features a latching spring 35, a latching wheel 36 and a base unit 37. The latching spring 35 is formed by a bent wire which is also embodied to be compatible with magnetic resonance. The latching spring 35 has a u-shaped part area 38 which is disposed in a center of the latching spring 35, and two end areas 39, 40, which are disposed in parallel to one another. The two end areas 39, 40 extend away from the u-shaped part area 38, wherein for this purpose an outer arm 41 of the u-shaped part area 38 is longer than an inner arm 42 of the u-shaped part area 38. An outer end area 39 is disposed in this case on the outer arm 41 of the u-shaped part area 38 and an inner end area 40 on the inner arm 42 of the u-shaped part area 38. The end areas 39, 40 are aligned at right angles to the two arms 41, 42 of the u-shaped part area 38. In addition the two end areas 39, 40 extend in a same direction away from the u-shaped part area 38, wherein the direction runs in parallel to a direction along a distance from the outer arm 41 to the inner arm 42. The two end areas 39, 40 and the u-shaped part area 38 are additionally arranged within one plane, so that the latching spring 35 is embodied flat (FIGS. 2 to 4 and 6).

The outer end area 39 also has a safety area 43, which is disposed at an end of the outer end area 39 facing away from the u-shaped part area 38. This safety area 43 is also disposed in a planar manner to the two arms 41, 42 and the two end areas 39, 40, wherein the safety area 43 makes an angle with the rest of the outer end area 39 of less than 165° and less than 160°. In addition the angle between the rest of the outer end area 39 and the safety area 43 is embodied greater than 90° greater than 120°. The safety area 43 also extends from the outer end area 39 in a direction of the inner end area 40 of the latching spring 35 away from the outer end area 39.

Figure 2:
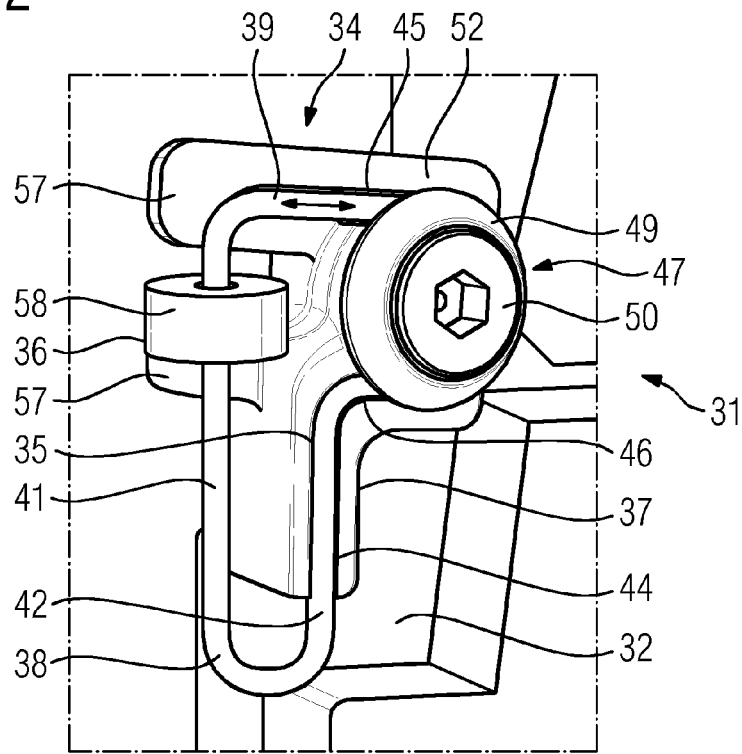
FIG. 2 shows a schematic of a first view of a disclosed latching apparatus.
Figure 3:
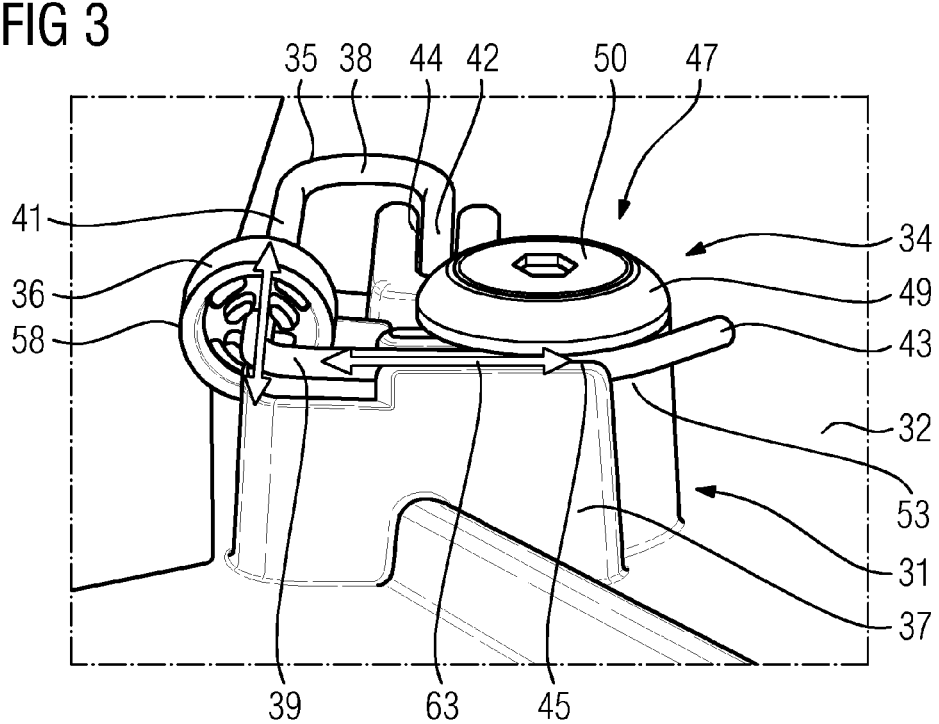
FIG. 3 shows a second view of the latching apparatus.
Figure 4:
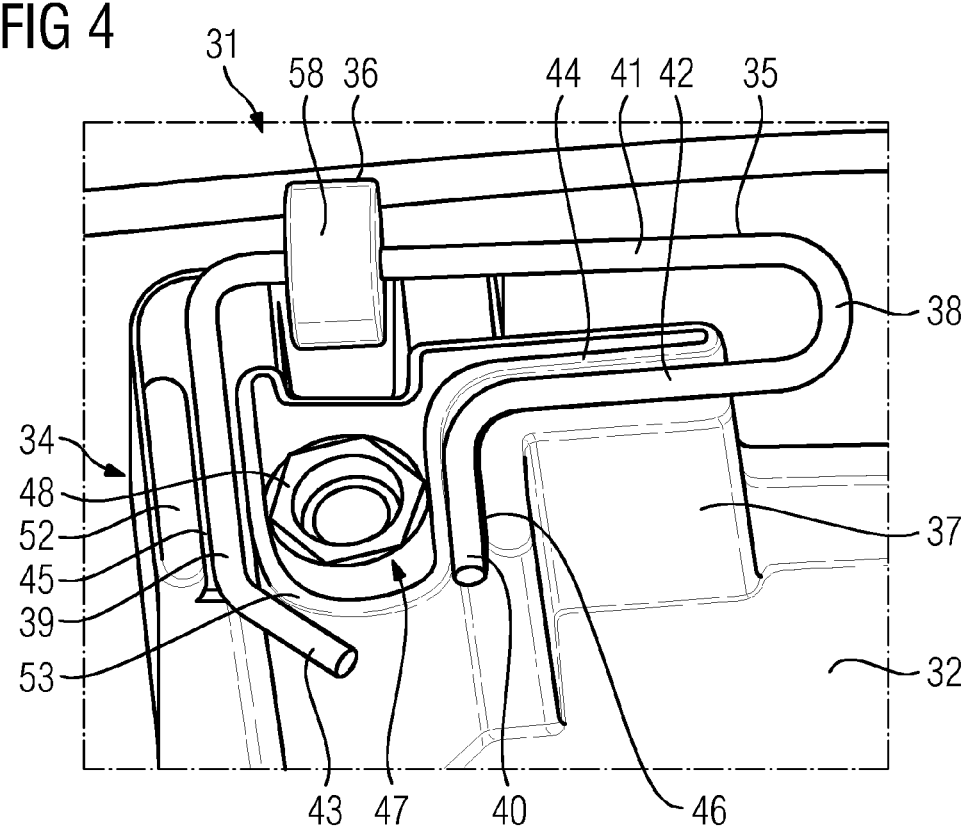
FIG. 4 shows a third view of the latching apparatus.

The base unit 37 of the latching unit 34 is designed to support the latching spring 35 on a first cladding component 32, FIGS. 2 to 4. To this end the base unit 37 is made of plastic for example and fixed to the first cladding component 32. The base unit 37 can be fixed to the first cladding component 32 in such cases by gluing the base unit 37 to the first cladding component 32. In addition it is also conceivable for the first cladding component 32 to already be manufactured in one piece with the base unit 37 by molding the base unit 37 onto the first cladding component 32 in one piece. In addition further base unit 37 fixings to the first cladding component 32 appearing sensible to the person skilled in the art are always conceivable.

To support the latching spring 35 the base unit 37 has a number of guide elements 44, 45, 46. A first guide element 44 is designed for fixed support of a part area of the latching spring 35, with the part area being formed in this case by the inner arm 42, which is disposed rigidly, immovably, within the first guide element 44. The first guide element 44 here is formed by a guide channel. A second guide element 45 is designed to provide mobile support for a part area of the latching spring 35, with the part area being formed here by the outer end area 39, which is supported movably within the second guide element 45. The second guide element 45 is likewise formed by a guide channel. The latching spring 35, such as the outer end area 39 can execute a latching movement for a latching connection along the second guide element 45 in this way. The first guide element 44 extends at right angles to the second guide element 45. In addition the base unit 37 has a third guide element 46 which is disposed in parallel to the second guide element 45 and is at a fixed position in the inner end area 40 of the latching spring 35. The third guide element 46 is likewise formed by a guide channel. The first guide element 44 changes into the third guide element 46, with the two guide elements 44, 46 being disposed at right angles to one another and being connected to each other by a guide curve. Because of this guide curve the latching spring 35 is rigidly fixed to the inner arm 42 and the inner end area 40 within the base unit 37 (FIGS. 2 to 4).

In addition the latching unit has an attachment unit 47, by which the latching spring 35 is attached to the base unit 37. The attachment unit 47 has a first attachment element 48, which is surrounded by the base unit 37 and which has an internal thread (refer to FIG. 4). The first attachment element 48 can for example be formed by a tubular nut which is disposed molded-in by the plastic within the base unit 37. The first attachment element 48 is disposed on the base unit 37 between the second guide element 45 and the third guide element 46.

The attachment unit 47 also has two further attachment elements which are formed by a safety washer 49 and a clamping screw 50. The safety washer 49 has an external diameter which is greater than the maximum distance 51 between the two end areas 39, 40 of the latching spring 35 so that the two end areas 39, 40 are covered by the safety washer 49 in an attachment position. In addition the safety washer 49 has a central opening to allow the passage of a threaded bolt of the clamping screw 50.

For attaching the latching spring 35 to the base unit 37, the latching spring 35 is first positioned on the base unit 37 in an attachment position. Subsequently the safety washer 49 is laid over the latching spring 35 in the area of the first attachment element 48, with the safety washer 49 resting on the inner end area 40 of the latching spring 35. The second guide element 45 of the base unit 37 for mobile support of the outer end area 39 of the latching spring 35 has a support element 52 on which the safety washer 49 rests and together with the base unit 37 forms the second guide element 45 embodied as a guide channel with a diameter which is greater than a cross-sectional surface of the latching spring 35 in the outer end area 39. For attachment the clamping screw 50 is subsequently screwed to the first attachment element 48 and in this way the inner end area 40 of the latching spring 35 is clamped between the third guide element 46 and the safety washer 49 so that this inner end area 40 is supported immovably.

The base unit 37 also has a securing element 53 which is formed by an edge of the second guide element 45 together with an enclosing housing of the first attachment element 48 formed by the base unit 37 (FIG. 4). This securing element 53 of the base unit 37 prevents the safety area 43 of the outer end area 39 of the latching spring 35 from being able to be introduced into the second guide element 45 during a latching movement of the latching spring 35.

Figure 5:
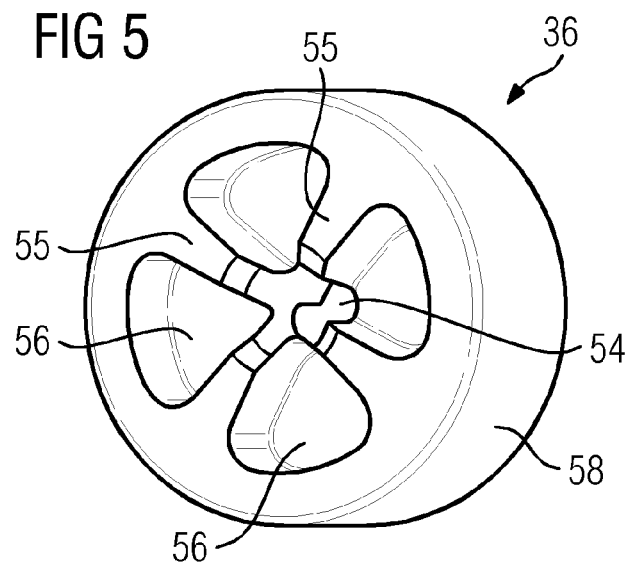
FIG. 5 shows a latching wheel of the latching apparatus.
Figure 6:
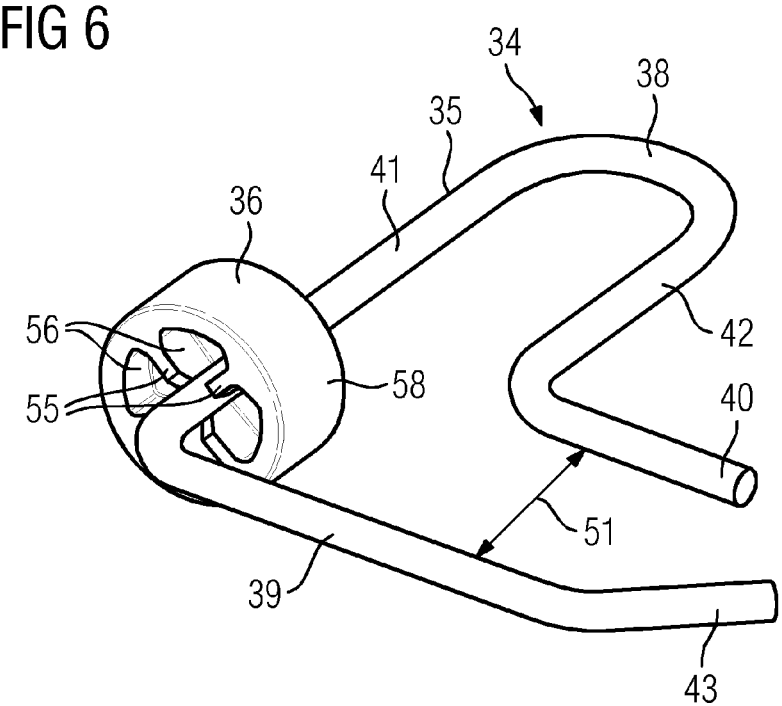
FIG. 6 shows the latching wheel together with the latching spring of the latching apparatus and FIG. 7 shows a housing section of housing cladding of the magnetic resonance apparatus.

The latching wheel 36 of the latching unit 34 is shown in greater detail in FIGS. 5 and 6. The latching wheel 36 has a central opening 54 by which the latching wheel 36 is supported movably on the latching spring 35. Around the central opening 54 the latching wheel 36 has spokes 55 and cutouts 56 which are disposed alternately to one another. In the present embodiment the latching wheel 36 has eight spokes 55 and eight cutouts 56, with four spokes 55 and four cutouts being disposed in each case on a latching disc surface of a latching disc of the latching wheel 36. The spokes 55 extend in each case from an edge area of the latching wheel 36 through to the central opening 54. The two latching disk surfaces are embodied the same or symmetrically in respect of an arrangement of the spokes 55 and cutouts 56. By the spokes 55 and the cutouts 56 a movement of the latching wheel 36 on the latching spring 35 in a longitudinal extent of the latching spring 35 is made possible. In a curved area and/or at the bends of the latching spring 35, the latching wheel 36, can be moved along the latching spring 35 because of the cutouts 56, so that an introduction and/or an installation of the latching wheel 36 on the already bent latching spring 35 is possible, in addition the central opening 34 of the latching wheel 36 also has a cross-sectional surface for this purpose which is slightly larger than the cross-sectional surface of the latching spring 35, so that the latching wheel 36 is prevented from tilting on the latching spring 35 during its introduction process.

The latching wheel 36 is disposed in an installed position on the latching spring 35 on the outer arm 41 of the u-shaped part area 38 of the latching spring 35. Here the latching wheel 36 is disposed at a height of an attachment unit 47 or a height between the outer end area 39 and the inner end area 40. So that the latching wheel 36 maintains its position along the outer arm 41, the base unit 37 has two positioning elements 57, which restrict a positional range of the latching wheel 36 on the latching spring 35 along the outer arm 41. Furthermore there can also be provision for a positioning of the latching wheel 36 on the latching spring 35, such as on the outer arm 41 of the latching spring 35, for the spokes 55 of the latching wheel 36 to rest at least partly on the latching spring 35 and in this way hold the latching wheel 36 in position. The latching wheel 36 also has an outer jacket surface which is formed by a sliding surface 58.

Figure 7:
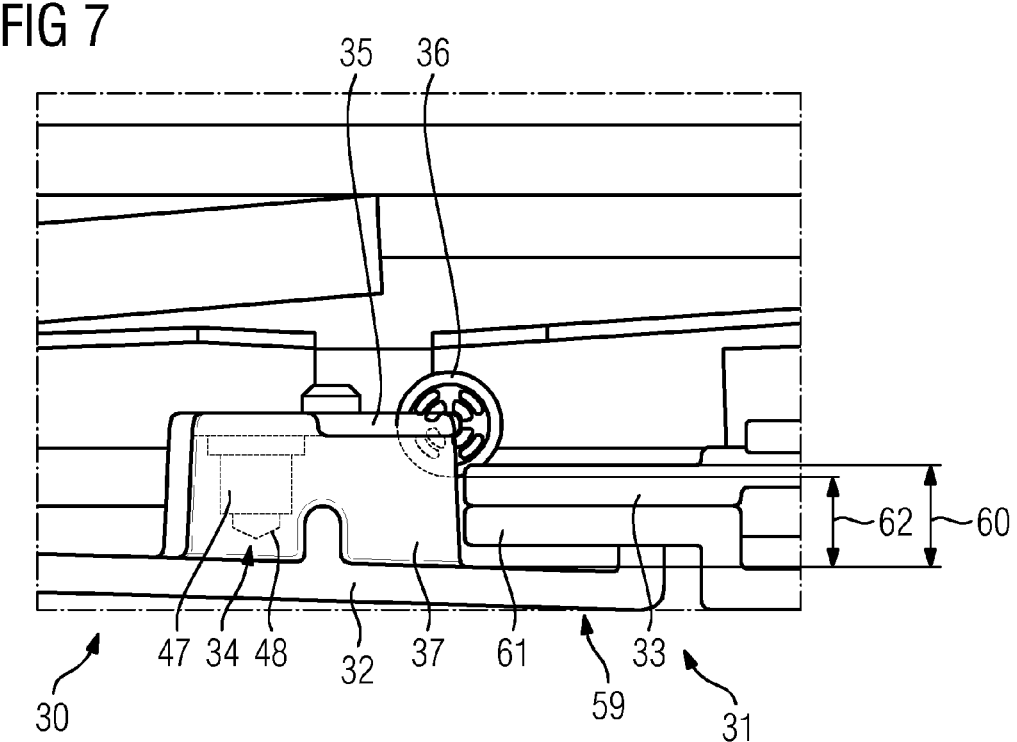

The base unit 37 is disposed on the first cladding component 32 such that the latching spring 35 fastened in the base unit 37 with the outer arm 41 and the latching wheel 36 disposed on the outer arm 41 face towards an edge area 59 of the first cladding component 32 for a latching connection with the second cladding component 33. The base unit 37 also has a height that is adapted to a distance 60 of an edge area 61 of the second cladding component 33 to a cladding surface of the first cladding component 32 facing towards the base unit 37 (FIG. 7). The distance 60 extends here from a side of the edge area 61 of the second cladding component 33 facing away from the first cladding component 32 to the cladding surface of the first cladding component facing towards the base unit 37. Here the base unit 37 is embodied such that the latching wheel 36 is at a minimum distance 62 to a cladding surface of the first cladding component 32 facing towards the base unit 37, which is smaller by approximately 30% and by approximately 10% of a radius of the latching wheel 36 than the distance 60 between the second cladding component 33 and the cladding surface of first cladding component 32.

For a latching connection between the latching unit 34 and the second cladding component 33, the second cladding component 33 is already installed on the housing cladding 30 of the magnetic resonance apparatus 10. The first cladding component 32 and the second cladding component 33 overlap in edge areas 59, 61 in an installed position on the housing cladding 30. The base unit 37 is installed on the first cladding component 32 such that in addition the latching unit 34, such as the latching wheel 36, overlaps with the edge area 61 of the second cladding component 33. Here the overlapping area is greater than 25% of a diameter of the latching wheel 36 and less than 50% of the diameter of the latching wheel 36.

During an introduction movement of the first cladding component 32 on the second cladding component 33 the latching wheel 36 rests on the edge area 61 of the second cladding component 33. The introduction movement of the first cladding component 32 here is at right angles to a cladding surface of the first cladding component 32 and aligned in a direction from a surface of the first cladding component 32 facing away from the latching unit 34 in a direction of a surface of the first cladding component 32 facing towards the latching unit 34.

If the first cladding component 32 is moved further along the introduction movement, a force must be applied here that is greater than the latching force of the latching spring 36, so that the latching spring 35 is moved in a direction 63 of the second guide element 45 in a direction from the latching wheel 36 towards the attachment unit 47. This movement is supported by the rotatable support of the latching wheel 36, with the latching wheel 36 being disposed rotatably on the latching spring 35 aligned around an axis that is parallel to a longitudinal extent of the outer arm 41 of the u-shaped part area 38 of the latching spring 35. During the introduction of the first cladding component 32 the latching wheel 36 is moved together with the outer arm 41 and the outer end area 39 in the direction 63 until a rim area of the edge area 61 of the second cladding components 33 facing away from the first cladding component 32 is disposed closer to the first cladding component 32 than one facing away from a center of the latching wheel 36. Subsequently, because of the latching force of the latching spring 35, the latching wheel 36 is moved together with the outer arm 41 and the outer end area 39 against the direction 63, so that the introduction movement of the first cladding component 32 is assisted. The latching wheel 36 rolls in this case partly over the edge area 61 of the second cladding component 33, so that the latching wheel 36 overlaps the edge area 61 of the second cladding component 33 and in this way, because of the latching force of the latching spring 35, holds the first cladding component 32 in position. Because of the spring force of the latching spring 35, the latching wheel 36 overlaps the end area 61 of the second cladding component 33 quickly, so that an installer, because of this latching movement of the latching spring 35, obtains feedback for secure latching.

In the present embodiment the latching spring 35 has a cross-sectional surface which is aligned at right angles to the longitudinal direction of the latching spring 35, of approximately 2.2 mm. With this cross-sectional surface the latching force of the latching spring 35 is embodied such that the latching unit 24 has a function supporting an attachment, so that a number of attachment elements, such as screws for example, can be minimized. If on the other hand the cross-sectional surface of the latching spring 35 is embodied about 10% thicker, a complete attachment can be achieved by the latching units 34 between the two cladding components 32, 33 and in such cases further attachment elements can be dispensed with entirely.

The latching unit 34 described in FIGS. 2 to 7 is embodied flat, so that it can be installed in a space between the housing cladding 30 and the magnet unit 11 without additional changes to the housing cladding 30. In addition the latching unit 34 embodied in this way is better in respect of transmission of vibrations because of the embodiment of the latching spring 36 and the play-free arrangement of the latching wheel 36 on the latching spring 35.

The invention claimed is:
1. A latching apparatus for housing cladding of a medical imaging apparatus, comprising:
   a first cladding component;
   a second cladding component; and
   a latching unit,
   wherein the latching unit is disposed on the first cladding component for a latching connection with the second cladding component,
   wherein the latching unit comprises a latching spring with a latching wheel,
   wherein the latching spring comprises a u-shaped part area and an inner end area and an outer end area that are disposed in parallel to one another and extend away from the u-shaped part area,
   wherein the inner end area is disposed on an inner arm of the u-shaped part area and the outer end area is disposed on an outer arm of the u-shaped part area,
   wherein the inner end area and the outer end area are aligned at right angles to the inner arm and the outer arm of the u-shaped part area respectively,
   wherein the latching wheel comprises an inner portion and an outer portion, the inner portion defining a central opening by which the latching wheel is supported movably along the latching spring, the outer portion defining an outer circumference configured to engage with the second cladding component to make the latching connection between the first cladding component and the second cladding component when the latching wheel is in a locking position,
   wherein a cross-sectional surface defining the central opening of the latching wheel is larger than a cross-sectional surface of the latching spring to prevent the latching wheel from titling on the latching spring during moving on a curved area of the latching spring,
   wherein the latching wheel comprises at least two cutouts around the central opening, the at least two cutouts defined between the inner portion and the outer portion, and
   wherein the at least two cutouts are configured to enable the latching wheel to move along the latching spring in the curved area during assembly of the latching unit.

2. The latching apparatus as claimed in claim 1, wherein the latching wheel is supported rotatably on the latching spring.

3. The latching apparatus as claimed in claim 1, wherein the latching wheel comprises at least two spokes connecting the inner portion and the outer portion, and wherein the at least two spokes and the at least two cutouts are disposed in a radial direction alternating around the central opening of the latching wheel to be attached to the latching spring.

4. The latching apparatus as claimed in claim 1, wherein the latching spring comprises a safety area which restricts a maximum latching movement of the latching spring.

5. The latching apparatus as claimed in claim 1, wherein the latching unit comprises a base unit for supporting the latching spring.

6. The latching apparatus as claimed in claim 5, wherein the base unit is fixed to the first cladding component.

7. The latching apparatus as claimed in claim 5, wherein the base unit comprises at least one first guide element for fixed support of at least one part area of the latching spring.

8. The latching apparatus as claimed in claim 5, wherein the base unit comprises at least one second guide element for mobile support of at least one part area of the latching spring.

9. The latching apparatus as claimed in claim 5, wherein the base unit has a height that is at least a distance between an edge area of the second cladding component and a cladding surface of the first cladding component facing towards the base unit.

10. The latching apparatus as claimed in claim 5, wherein the base unit comprises at least one positioning element for positioning the latching wheel on the latching spring.

11. The latching apparatus as claimed in claim 1, wherein the latching wheel comprises an overlap area with the second cladding component when the latching wheel is in the locking position, and wherein the overlap area is greater than 25% of an external diameter of the latching wheel and is less than 50% of the external diameter of the latching wheel.

12. The latching apparatus as claimed in claim 1, wherein the latching unit comprises a capability of being compatible with magnetic resonance.

13. A housing cladding for a medical imaging device, comprising:
   a latching apparatus that is enclosed by the housing cladding, wherein the latching apparatus comprises:
      a first cladding component;
      a second cladding component; and
      a latching unit,
      wherein the latching unit s disposed on the first cladding component for a latching connection with the second cladding component,
      wherein the latching unit comprises a latching spring with a latching wheel,
      wherein the latching spring comprises a u-shaped part area and an inner end area and an outer end area that are disposed in parallel to one another and extend away from the u-shaped part area,
      wherein the inner end area is disposed on an inner arm of the u-shaped part area and the outer end area is disposed on an outer arm of the u-shaped part area,
      wherein the inner end area and the outer end area are aligned at right angles to the inner arm and the outer arm of the u-shaped part area respectively,
      wherein the latching wheel comprises an inner portion and an outer portion, the inner portion defining a central opening by which the latching wheel is supported movably along the latching spring, the outer portion defining an outer circumference configured to engage with the second cladding component to make the latching connection between the first cladding component and the second cladding component when the latching wheel is in a locking position,
      wherein a cross-sectional surface defining the central opening of the latching wheel is larger than a cross-sectional surface of the latching spring to prevent the latching wheel from titling on the latching spring during moving on a curved area of the latching spring,
      wherein the latching wheel comprises at least two cutouts around the central opening, the at least two cutouts defined between the inner portion and the outer portion, and
      wherein the at least two cutouts are configured to enable the latching wheel to move along the latching spring in the curved area during assembly of the latching unit.

14. A medical imaging device, comprising:
   a magnet unit; and
   a housing cladding that surrounds the magnet unit,
   wherein the housing cladding comprises a latching apparatus that s enclosed by the housing cladding,
   wherein the latching apparatus comprises:
      a first cladding component;
      a second cladding component; and
      a latching unit,
      wherein the latching unit is disposed on the first cladding component for a latching connection with the second cladding component,
      wherein the latching unit comprises a latching spring with a latching wheel,
      wherein the latching spring comprises a u-shaped part area and an inner end area and an outer end area that are disposed in parallel to one another and extend away from the u-shaped part area,
      wherein the inner end area is disposed on an inner arm of the u-shaped part area and the outer end area is disposed on an outer arm of the u-shaped part area,
      wherein the inner end area and the outer end area are aligned at right angles to the inner arm and the outer arm of the u-shaped part area respectively,
      wherein the latching wheel comprises an inner portion and an outer portion, the inner portion defining a central opening by which the latching wheel is supported movably along the latching spring, the outer portion defining an outer circumference configured to engage with the second cladding component to make the latching connection between the first cladding component and the second cladding component when the latching wheel is in a locking position,
      wherein a cross-sectional surface defining the central opening of the latching wheel is larger than a cross-sectional surface of the latching spring to prevent the latching wheel from titling on the latching spring during moving on a curved area of the latching spring,
      wherein the latching wheel comprises at least two cutouts around the central opening, the at least two cutouts defined between the inner portion and the outer portion, and
      wherein the at least two cutouts are configured to enable the latching wheel to move along the latching spring in the curved area during assembly of the latching unit.

* * * * *